(12) United States Patent
Kunz et al.

(10) Patent No.: US 8,779,152 B2
(45) Date of Patent: Jul. 15, 2014

(54) METHODS FOR PREPARING RUTHENIUM CARBENE COMPLEX PRECURSORS AND RUTHENIUM CARBENE COMPLEXES

(75) Inventors: Linda A. Kunz, Naperville, IL (US); Steven A. Cohen, Naperville, IL (US); Melvin L. Luetkens, Jr., Batavia, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 201 days.

(21) Appl. No.: 13/272,788

(22) Filed: Oct. 13, 2011

(65) Prior Publication Data

US 2013/0096313 A1 Apr. 18, 2013

(51) Int. Cl.
*C07F 15/00* (2006.01)

(52) U.S. Cl.
CPC ......... *C07F 15/0046* (2013.01); *C07F 15/0053* (2013.01)
USPC ............................. 548/103; 556/23; 556/46

(58) Field of Classification Search
CPC .................. C07F 15/0046; C07F 15/0053
USPC ........................... 548/103; 556/23, 46
See application file for complete search history.

(56) References Cited

U.S. PATENT DOCUMENTS

| 5,324,850 A | 6/1994 | Juge et al. |
| 7,329,758 B1 | 2/2008 | Grubbs et al. |

FOREIGN PATENT DOCUMENTS

EP 1 375 506 A1 1/2004

OTHER PUBLICATIONS

Unknown author, Gmelins Handbuch Der Anorganischen Chemie, System-Nummer 63, Ruthenium, Erganzungsband, Verlag Chemie, GmbH, Weinheim, 1970, pp. 82,284-294,302-312 and 426 (partial translation).*
Albers, Michael O., et al., ($\eta^4$-1, 5-Cyclooctadiene)Ruthenium(II)Complexes, Inorganic Syntheses, 1989, 26, pp. 68-77.
Albers, Michael O, et al., "Dinuclear Ruthenium(II) Carboxylate Complexes", *Inorganic Syntheses*, 1989, 26, 249-258.
Bernardis, Francesco L., et al., "*A Review of Methods of Separation of the Platinum-Group Metals Through Their Chloro-Complexes*", Reactive & Functional Polymers, 2005, 65, pp. 205-217.
Deloume, Par Jean-Pierre, et al., "*Nouvelle Determination de la Structure Cristalline du µ-Oxo-bis[pentachlororuthenate-(IV) de Potassium, $K^4[Ru_2\ Cl_{10}O]$, et Affinement de la Structure de l'Hexachlororuthenate de Potassium, $K_2[RuCl_6]$*"Acta Cryst. B, 1979, 35, pp. 558-561 (translation).
Emel'yanov, V.A., et al., "Crystal Structure of Ammonium Pentachloro-Aquaruthenate(III) $(NH_4)_2$ [$Ru(H_2O)Cl_5$]", *J. of Structural Chemistry*, 2008, 49, pp. 585-588 (translation).
Hallman, P.S., et al., "*Tetrakis (Triphenyiphosphine)Dichloro-Ruthenium(II) and Tris(Triphenylphosphine)-Dichlororuthenium(II)*", Inorganic Syntheses, 1970, 12, pp. 237-240.
Schwab, Peter, et al., "*Synthesis and Applications of $RuCl_2(=CHR')(PR_3)_2$: The influence of the Alkylidene Moiety on Metathesis Activity*", J. Am. Chem. Soc., 1996, 118, pp. 100-110.
Weir, Ron D., et al., "*Thermodynamics, Phase Transitions and Crystal Structure of Ammonium Hexahalides: Comparative Study of the Heat Capacity and Thermodynamic Properties of $(NH_4)_2PtCl_6$, $(ND_4)_2PtCl_6$, $(NH_4)_2PtBr_6$, $(ND_4)_2PtBr_6$, $(NH_4)_2PdCl_6$, $(ND_4)_2PdCl_6$, $(NH_4)_2TeCl_6$, $(ND_4)_2TeCl_6$, and $(NH_4)_2RuCl_6$ from 5K to 350 $K^{a\prime\prime}$*, J. Chem. Thermodynamics, 2002, 34, pp. 133-153.
Wilhelm, Thomas E., et al., "*Reactivity of $Ru(H)(H2)Cl(PCy_3)$ with Propargyl and Vinyl Chlorides: New Methodology to Give Metathesis-Active Ruthenium Carbenes*", Organometallics, 1997, 16, No. 18, pp. 3867-3869.
Abstracts of CAPLUS Search Results (26 pages total).
Linn, Donald E., "Micropreparation of [$RuH_2(PPh_3)_4$]," Journal of Chemical Education, vol. 76, No. 11, Nov. 1999, pp. 1484-1485.
Madec, J. et al., "Asymmetric hydrogenation reactions using a practical in situ generation of chiral ruthenium-diphosphine catalysts from anhydrous $RuCl_3$," Tetrahedron, vol. 57, 2001, pp. 2563-2568.
Schrodi, Yann et al., "Evolution and Applications of Second-Generation Ruthenium Olefin Metathesis Catalysts," Aldrichimica Acta, vol. 40, No. 2, 2007, pp. 45-52.
Unknown author, Colonial Metals, Inc., Product Information, © 2009, retrieved online Jun. 6, 2013, 7 pages.
International Search Report and Written Opinion of the International Searching Authority for International Application No. PCT/US2012/059280, dated May 13, 2013, 18 pages.
Bellaloui, Achour et al., "Preparation and characterization of $RuS_2$ and its catalytic properties in biphenyl hydrogenation," C.R. Acad. Sci. Paris, t. 307, Series II, 1988, pp. 1171-1176 (partial translation).
Scholl, M. et al., "Synthesis and Activity of a New Generation of Ruthenium-Based Olefin Metathesis Catalysts Combined with 1,3-Dimesityl-4,5-Dihydroimidazol-2-Yliden E Ligands," Organic Letters, American Chemical Society, vol. 1, No. 6, Jan. 1999, pp. 953-956.
Unknown author, Gmelins Handbuch Der Anorganischen Chemie, System-Nummer 63, Ruthenium, Erganzungsband, Verlag Chemie, GmbH, Weinheim, 1970, pp. 82, 284-294, 302-312 and 426 (partial translation).
Partial International Search Report for International Application No. PCT/US2012/059280, dated Jan. 22, 2013, 2 pages.

* cited by examiner

*Primary Examiner* — Joseph Kosack
(74) *Attorney, Agent, or Firm* — Brinks Gilson & Lione

(57) ABSTRACT

A method for preparing a ruthenium carbene complex precursor includes reacting a ruthenium refinery salt with a hydrogen halide to form a ruthenium intermediate, and reacting the ruthenium intermediate with an L-type ligand to form the ruthenium carbene complex precursor. A method for preparing a ruthenium vinylcarbene complex includes converting a ruthenium carbene complex precursor into a ruthenium hydrido halide complex, and reacting the ruthenium hydrido halide complex with a propargyl halide to form the ruthenium vinylcarbene complex. A method for preparing a ruthenium carbene complex includes converting a ruthenium carbene complex precursor into a ruthenium carbene complex having a structure $(PR^1R^2R^3)_2Cl_2Ru=CH-R^4$, wherein $R^1$, $R^2$, $R^3$, and $R^4$ are alike or different, and wherein covalent bonds may optionally exist between two or more of $R^1$, $R^2$, and $R^3$.

78 Claims, 6 Drawing Sheets

FIG. 2

REFINERY B SALT

$(NH_4)_2RuCl_5 \cdot H_2O$
$(NH_4)_4[Ru_2OCl_{10}]$
$NH_4Cl$

↓ sublimation
   $-NH_4Cl$ $(NH_4)_2RuCl_5 \cdot H_2O$
$(NH_4)_4[Ru_2OCl_{10}]$

REFINERY A SALT

$(NH_4)_4[Ru_2OCl_{10}]$

↘ HCl        ↙ HCl $(NH_4)_2RuCl_6$

↓ 1) 2 COD, EtOH, reflux, $N_2$
   2) Wash with $H_2O$ $[RuCl_2(COD)]_x$

FIG. 4

REFINERY B SALT $(NH_4)_2RuCl_5 \cdot H_2O$
$(NH_4)_4[Ru_2OCl_{10}]$
$NH_4Cl$

↓ sublimation
   $-NH_4Cl$ $(NH_4)_2RuCl_5 \cdot H_2O$
$(NH_4)_4[Ru_2OCl_{10}]$

REFINERY A SALT $(NH_4)_4[Ru_2OCl_{10}]$

↘ HCl     ↙ HCl $(NH_4)_2RuCl_6$

↓ 3 $PPh_3$ $RuCl_2(PPh_3)_3$

METHODS FOR PREPARING RUTHENIUM CARBENE COMPLEX PRECURSORS AND RUTHENIUM CARBENE COMPLEXES

TECHNICAL FIELD

The present teachings relate generally to ruthenium carbene complex precursors and preparations thereof, as well as to the use of such precursors in the preparation of ruthenium carbene complexes.

BACKGROUND

With the development of new, relatively air-stable transition metal carbene complex catalysts—particularly ones exhibiting increased tolerance towards common organic functional groups—the olefin metathesis reaction has established itself as one of the most powerful reactions in the synthetic preparation of alkenes.

Ruthenium carbene complexes—for example, the "first-generation" and "second generation" Grubbs-type catalysts developed by Nobel laureate Robert H. Grubbs—are especially popular and versatile catalysts for use in olefin metathesis. The polymeric di-$\mu$-chloro($\eta^4$-1,5-cyclooctadiene)ruthenium(II)—represented herein as $[RuCl_2(COD)]_x$—and the monomeric tris(triphenylphosphine)ruthenium(II) chloride—represented herein as $RuCl_2(PPh_3)_3$—are precursors in the synthesis of Grubbs-type ruthenium carbene complexes.

As shown in FIG. 1, $[RuCl_2(COD)]_x$ (*Inorganic Syntheses*, 1989, 29, 68-77) and $RuCl_2(PPh_3)_3$ (*Inorganic Syntheses*, 1970, 12, 237-240) are typically prepared starting from $RuCl_3.nH_2O$. The ruthenium trichloride is itself prepared starting from low cost ruthenium refinery salts (e.g., ammonium salts of ruthenium-chloro complexes produced in the refining of natural platinum group metal deposits and recycled platinum group metals). However, since the ruthenium refinery salts are first converted to ruthenium metal, which in turn is then oxidized to Ru(III), the preparations of $[RuCl_2(COD)]_x$ and $RuCl_2(PPh_3)_3$ via the intermediacy of ruthenium trichloride are costly and inefficient.

A more efficient and less costly preparation of $[RuCl_2(COD)]_x$, $RuCl_2(PPh_3)_3$, and analogous $MX_2L_q$ ruthenium carbene complex precursors from ruthenium refinery salts—particularly one that does not require the intermediacy of ruthenium trichloride—is desirable.

SUMMARY

The scope of the present invention is defined solely by the appended claims, and is not affected to any degree by the statements within this summary.

By way of introduction, a first method for preparing a ruthenium carbene complex precursor in accordance with the present teachings includes (a) reacting a ruthenium refinery salt with a hydrogen halide to form a ruthenium intermediate, and (b) reacting the ruthenium intermediate with an L-type ligand to form the ruthenium carbene complex precursor.

A second method for preparing a ruthenium carbene complex precursor in accordance with the present teachings includes (a) reacting a ruthenium refinery salt with a hydrogen halide to form a ruthenium intermediate, and (b) reacting the ruthenium intermediate with cyclooctadiene and/or a phosphorous-containing material having a structure $PR^1R^2R^3$ to form the ruthenium carbene complex precursor. The ruthenium refinery salt includes a material selected from the group consisting of $(NH_4)_2RuCl_5$, $(NH_4)_2RuCl_5.H_2O$, polyhydrated $(NH_4)_2RuCl_5$, $(NH_4)_4[Ru_2OCl_{10}]$, and combinations thereof. The ruthenium intermediate includes a compound selected from the group consisting of $(NH_4)_2RuX^1_6$, $(NH_4)_2RuX^1_yX^2_{6-y}$, wherein y is an integer value from 1 to 5, and a combination thereof. The ruthenium carbene complex precursor includes a compound having a structure $[RuX^3X^4(COD)]_x$, wherein x is an integer value of 1 or more, and/or a compound having a structure $RuX^5X^6(PR^1R^2R^3)_3$, wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. Covalent bonds may optionally exist between two or more of $R^1$, $R^2$, and $R^3$, such that when two or more of $R^1$, $R^2$, and $R^3$ are taken together, a bidentate ligand to phosphorous is formed. $X^1$, $X^2$, $X^3$, $X^4$, $X^5$, and $X^6$ are halogen atoms that are each independently selected from the group consisting of F, Cl, Br, and I with a caveat that $X^1$ and $X^2$ are different.

A first method for preparing a ruthenium vinylcarbene complex in accordance with the present teachings includes (a) converting a ruthenium carbene complex precursor prepared according to a method described above into a ruthenium hydrido halide complex, and (b) reacting the ruthenium hydrido halide complex with a propargyl halide to form the ruthenium vinylcarbene complex.

A method for preparing a ruthenium carbene complex in accordance with the present teachings includes converting a ruthenium carbene complex precursor prepared according to a method described above into a ruthenium carbene complex having a structure $(PR^1R^2R^3)_2X^1X^2Ru=CH-R^4$. $X^1$ and $X^2$ are halogen atoms that are each independently selected from the group consisting of F, Cl, Br, and I. $R^1$, $R^2$, $R^3$, and $R^4$ are alike or different, and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. Covalent bonds may optionally exist between two or more of $R^1$, $R^2$, and $R^3$, such that when two or more of $R^1$, $R^2$, and $R^3$ are taken together, a bidentate ligand to phosphorous is formed.

BRIEF DESCRIPTION OF THE DRAWINGS

FIG. 2 shows a synthetic scheme for converting ruthenium refinery salts to $[RuCl_2(COD)]_x$ in accordance with the present teachings.

FIG. 4 shows a synthetic scheme for converting ruthenium refinery salts to $RuCl_2(PPh_3)_3$ in accordance with the present teachings.

DETAILED DESCRIPTION

Figure 1:
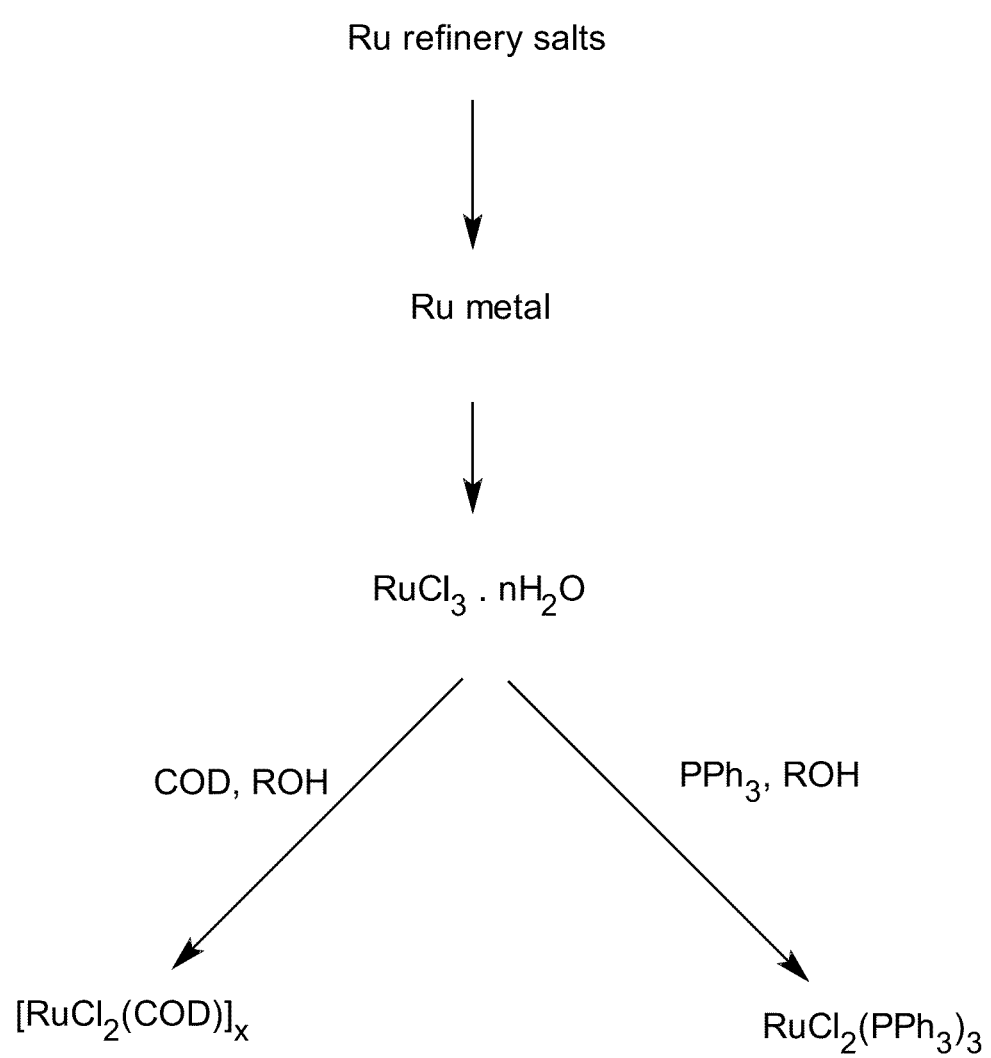
FIG. 1 shows a synthetic scheme for converting ruthenium refinery salts to $[RuCl_2(COD)]_x$ and $RuCl_2(PPh_3)_3$ by conventional methodologies.

A facile synthetic route to ruthenium carbene complex metathesis catalyst precursors—such as $[RuCl_2(COD)]_x$, $RuCl_2(PPh_3)_3$, and analogous $MX_2L_q$ complexes (e.g., where q is an integer from 1 through 4)—has been discovered and is described herein. As shown in FIGS. 2 and 4, the inventive route starts from low-cost ruthenium refinery salts and does not require any conversion of these salts to ruthenium metal or subsequent oxidation of ruthenium metal to $RuCl_3$—two of the principal drawbacks associated with the conventional synthetic preparations of $RuCl_2(COD)]_x$, $RuCl_2(PPh_3)_3$, and analogous complexes.

Definitions

Throughout this description and in the appended claims, the following definitions are to be understood:

The phrase "ruthenium refinery salt" refers generally to a ruthenium- and halogen-containing material. It is to be understood that a "ruthenium refinery salt" as defined herein may further comprise additional elements besides ruthenium and halogen, including but not limited to oxygen. Representative examples of "ruthenium refinery salts" include but are not limited to materials obtained from—or substantially chemically equivalent to what could otherwise be obtained from— the processing of a natural platinum group metal (PGM) deposit, as well as materials obtained from alternative chemical sources (e.g., ammoniated ruthenium oxychloride aka ruthenium red, etc.) and/or from recovery and/or reclamation processing of a ruthenium-containing material used in a prior chemical reaction. In some embodiments, a "ruthenium refinery salt" is obtained from a natural PGM deposit by a technique as described in *Reactive & Functional Polymers*, 2005, 65, 205-217.

The phrase "ruthenium intermediate" refers to a ruthenium-containing material that is obtained from but is chemically different than a ruthenium refinery salt that was subjected to a reaction involving a hydrogen halide.

The phrase "L-type ligand" refers to a two-electron neutral ligand. Representative examples of an "L-type ligand" for use in accordance with the present teachings include but are not limited to olefins, phosphines, phosphites, amines, carbon monoxide (CO), nitrogen ($N_2$), and the like, and combinations thereof.

The term "olefin" refers to a hydrocarbon compound containing at least one carbon-carbon double bond. As used herein, the term "olefin" encompasses straight, branched, and/or cyclic hydrocarbons having only one carbon-carbon double bond (e.g., monoenes) as well as more than one carbon-carbon double bond (e.g., dienes, trienes, etc.). In some embodiments, the olefin is functionalized.

The term "functionalized" as used in reference to an olefin refers to the presence of one or more heteroatoms, wherein the heteroatom is an atom other than carbon and hydrogen. In some embodiments, the heteroatom constitutes one atom of a polyatomic functional group with representative functional groups including but not limited to carboxylic acids, carboxylic esters, ketones, aldehydes, anhydrides, sulfur-containing groups, phosphorous-containing groups, amides, imides, N-containing heterocycles, aromatic N-containing heterocycles, salts thereof, and the like, and combinations thereof.

The term "hydrothermal" used in connection with reactions, conversions, treatments, and the like refers to reaction conditions within a substantially "closed" reaction system— typically though not necessarily a system in which pressure and/or temperature exceed atmospheric conditions—such as may be achieved in a Parr-type reactor.

The term "atmospheric" used in connection with reactions, conversions, treatments, and the like refers to reaction conditions within an "open" (as opposed to closed) reaction system. It is to be understood that "atmospheric" in the sense used herein does not preclude the introduction into a reaction vessel of an inert atmosphere (e.g., a blanket of an inert gas) to replace or exclude air. Moreover, it is to be further understood that in an open reaction system, an internal temperature and/or pressure within the reaction vessel may exceed the ambient temperature and/or pressure outside the reaction vessel (in other words, "atmospheric" as used herein is not necessarily synonymous with "ambient" although, in some embodiments, it may be).

It is to be understood that elements and features of the various representative embodiments described below may be combined in different ways to produce new embodiments that likewise fall within the scope of the present teachings.

By way of general introduction, a method for preparing a ruthenium carbene complex precursor in accordance with the present teachings comprises reacting a ruthenium refinery salt with a hydrogen halide to form a ruthenium intermediate, and reacting the ruthenium intermediate with an L-type ligand to form the ruthenium carbene complex precursor.

In some embodiments, the hydrogen halide is provided as a gas. In some embodiments, the hydrogen halide is provided in solution. In some embodiments, the hydrogen halide is provided as an aqueous solution. In some embodiments, the hydrogen halide is selected from the group consisting of hydrogen chloride, hydrogen bromide, hydrogen fluoride, hydrogen iodide, and combinations thereof. In some embodiments, the hydrogen halide is selected from the group consisting of hydrogen chloride, hydrogen bromide, hydrogen iodide, and combinations thereof. In some embodiments, the hydrogen halide is selected from the group consisting of hydrogen chloride, hydrogen bromide, and a combination thereof. In some embodiments, the hydrogen halide comprises hydrogen chloride. In some embodiments, the hydrogen halide comprises an aqueous solution of hydrogen chloride (e.g., hydrochloric acid). In some embodiments, the hydrogen halide comprises hydrogen bromide. In some embodiments, the hydrogen halide comprises an aqueous solution of hydrogen bromide (e.g., hydrobromic acid).

In some embodiments, the L-type ligand is selected from the group consisting of olefins, phosphines, phosphites, amines, CO, $N_2$, and combinations thereof. In some embodiments, the L-type ligand is selected from the group consisting of olefins, phosphines, and a combination thereof.

In some embodiments, the L-type ligand comprises an olefin. In some embodiments, the olefin is selected from the group consisting of monoenes, dienes, trienes, and combinations thereof. In some embodiments, the olefin is acyclic. In some embodiments, the olefin comprises an acyclic C6 or greater monoene. In some embodiments, the olefin comprises an acyclic diene with representative acyclic dienes including but not limited to 1,5-hexadiene, 2,6-octadiene, and the like, and combinations thereof. In some embodiments, the olefin is cyclic. In some embodiments, the olefin comprises a cyclic diene with representative cyclic dienes including but not limited to cyclohexadiene, cycloheptadiene, cyclooctadiene, cyclononadiene, cyclodecadiene, cycloundecadiene, cyclododecadiene, paramenthadiene, phellandrene, norbornadiene, terpinene, limonene, and the like, and combinations thereof. In some embodiments, the olefin comprises an acyclic triene. In some embodiments, the olefin comprises a cyclic triene with a representative cyclic triene including but not limited to cyclododecatriene. In some embodiments, the olefin is aromatic with representative aromatic olefins including but not limited to cyclopentadiene, benzene, toluene, o-xylene, m-xylene, p-xylene, mesitylene, and the like, and combinations thereof.

In some embodiments, the L-type ligand comprises a phosphorous-containing ligand (e.g., phosphines, phosphites, and the like, and combinations thereof). In some embodiments, the phosphorous-containing ligand comprises a structure $PR^1R^2R^3$, wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. In some embodiments, covalent bonds may optionally exist between two or more of $R^1$, $R^2$, and $R^3$, such that when two or more of $R^1$, $R^2$, and $R^3$ are taken together, a bidentate ligand to phosphorous is formed. In some embodiments, the phosphorous-containing ligand comprises a phosphine. In some embodiments, the phosphine comprises a trialkyl phosphine. In some embodiments, the phosphine comprises triphenyl phosphine. In some embodiments, the phosphorous-containing ligand comprises a phosphite.

The chemical composition of a particular ruthenium refinery salt for use in accordance with the present teachings can differ according to the specific refinery that produced it and/or the exact methodology used by that refinery in procuring the ruthenium from a natural PGM deposit. Moreover, it is to be understood that a ruthenium refinery salt in accordance with the present teachings can include one or more impurities—including but not limited to Ru metal, $NH_4Cl$, and the like, and combinations thereof—that are either removed, either partially or completely, prior to reacting the ruthenium refinery salt with hydrogen halide, or else carried along, either in whole or in part, for the reaction with hydrogen halide. For embodiments in which one or more impurity (e.g., Ru metal, $NH_4Cl$, etc.) is not completely removed from the ruthenium refinery salt prior to reacting the ruthenium refinery salt with hydrogen halide, at least a portion of the one or more impurity may be carried over into the resultant ruthenium intermediate which, in some embodiments, may itself be further contaminated by the presence of unreacted starting material (e.g., $(NH_4)_4[Ru_2OCl_{10}]$, etc.). In such instances, the one or more impurity and/or unreacted starting material can be removed, either partially or completely, prior to reacting the ruthenium intermediate with an L-type ligand to form the ruthenium carbene complex precursor or else carried along, either in whole or in part, for the reaction with an L-type ligand.

In some embodiments, a ruthenium refinery salt in accordance with the present teachings comprises one or a plurality of halide ligands and/or one or a plurality of ammonium cations. In some embodiments, a ruthenium refinery salt in accordance with the present teachings comprises one or a plurality of chloride ligands and/or one or a plurality of ammonium cations. In some embodiments, a ruthenium refinery salt for use in accordance with the present teachings is one produced by Refinery A. In some embodiments, the ruthenium refinery salt is one produced by Refinery B. In some embodiments, the ruthenium refinery salt is a combination of a material produced by Refinery A and a material produced by Refinery B.

As further described in Examples 1 and 2 below, x-ray powder diffraction (XRD) analysis of representative ruthenium refinery salts purchased, respectively, from Refinery A and Refinery B was performed. The XRD analysis of a representative ruthenium refinery salt obtained from Refinery B revealed the following composition: $(NH_4)_4[Ru_2OCl_{10}]$ (36.4 wt %), $(NH_4)_2RuCl_5.H_2O$ (13.9 wt %), and $NH_4Cl$ (49.3 wt %). By contrast to the large weight percentage of $NH_4Cl$ impurity identified in the Refinery B sample, an XRD analysis of a representative ruthenium refinery salt obtained from Refinery A revealed the following composition: $(NH_4)_4[Ru_2OCl_{10}]$ (96.1 wt %) and Ru metal impurity (3.9 wt %).

In some embodiments, a ruthenium refinery salt for use in accordance with the present teachings comprises a material selected from the group consisting of $(NH_4)_2RuCl_5$, $(NH_4)_2RuCl_5.H_2O$, polyhydrated $(NH_4)_2RuCl_5$, $(NH_4)_4[Ru_2OCl_{10}]$, and combinations thereof. In some embodiments, a ruthenium refinery salt for use in accordance with the present teachings comprises $(NH_4)_4[Ru_2OCl_{10}]$. In some embodiments, the ruthenium refinery salt further comprises an $NH_4Cl$ impurity which, in some embodiments, is residual reagent left over from a ruthenium recovery process (e.g., when $NH_4Cl$ is added to solution to precipitate pentachloro ruthenium species).

In some embodiments, the method in accordance with the present teachings further comprises removing at least a portion of the excess $NH_4Cl$ (if present) from the ruthenium refinery salt prior to reacting the ruthenium refinery salt with the hydrogen halide. Although pre-removal of excess $NH_4Cl$ is not essential, in some embodiments it is desirable inasmuch as higher yields are generally achievable when excess $NH_4Cl$ has been removed. In some embodiments, at least a portion of the $NH_4Cl$ impurity is removed via sublimation. In some embodiments, at least a portion of sublimed $NH_4Cl$ is removed from the remaining ruthenium refinery salt prior to reacting the remaining ruthenium refinery salt with the hydrogen halide.

In some embodiments, the ruthenium refinery salt used in accordance with the present teachings is a Refinery A sample inasmuch as it does not contain a significant amount of $NH_4Cl$ impurity that would warrant the extra step of its removal. It is to be understood that while the methods described herein have been demonstrated using ruthenium refinery salts from two different refineries—Refinery A and Refinery B—the present teachings can also be applied to ruthenium refinery salts from other refineries as well without limitation.

In some embodiments, the reacting of a ruthenium refinery salt with a hydrogen halide to form a ruthenium intermediate comprises a hydrothermal treatment. In some embodiments, the reacting is performed in a closed system. In some embodiments, a reaction temperature in the closed system is at least about 100° C. In some embodiments, a reaction temperature in the closed system is at least about 120° C. In some embodiments, a reaction temperature in the closed system is at least about 130° C. In some embodiments, a reaction temperature in the closed system is at least about 140° C. In some embodiments, a reaction temperature in the closed system is at least about 150° C. In some embodiments, a reaction temperature in the closed system is at least about 160° C. In some embodiments, a reaction temperature in the closed system is at least about 170° C. In some embodiments, a reaction temperature in the closed system is at least about 175° C. In some embodiments, a reaction temperature in the closed system is at least about 180° C.

Although the use of a gaseous hydrogen halide has been contemplated for some embodiments of the present teachings (for both hydrothermal and atmospheric conversions of ruthenium refinery salt to ruthenium intermediate), it is presently believed that the use of gaseous reagent may be less practical and/or slower than the use of a corresponding liquid acid reagent. Thus, in some embodiments, the hydrogen halide is provided in solution. In some embodiments, the hydrogen halide is provided in an aqueous solution.

In some embodiments, the hydrogen halide comprises hydrogen chloride which, in some embodiments, is provided in aqueous solution as hydrochloric acid. In some embodiments, the hydrochloric acid has a concentration of at least about 3 M or higher. In some embodiments, the hydrochloric acid has a concentration of at least about 4 M or higher. In some embodiments, the hydrochloric acid has a concentration of at least about 5 M or higher. In some embodiments, the hydrochloric acid has a concentration of at least about 6 M or higher. In some embodiments, the hydrochloric acid has a concentration of at least about 7 M or higher. In some embodiments, the hydrochloric acid has a concentration of at least about 8 M or higher. In some embodiments, the hydrochloric acid has a concentration of at least about 9 M or higher. In some embodiments, the hydrochloric acid is concentrated hydrochloric acid.

In some embodiments, the hydrogen halide comprises hydrogen bromide which, in some embodiments, is provided in aqueous solution as hydrobromic acid. In some embodiments, the ruthenium intermediate formed by reacting a ruthenium refinery salt with hydrogen bromide comprises one or a plurality of ammonium cations and/or one or a plurality of bromide ligands. In some embodiments, the ruthenium intermediate comprises a compound having a structure $(NH_4)_2RuBr_6$. In some embodiments, the ruthenium intermediate comprises a compound having a structure $(NH_4)_2RuBr_6$ and/or $(NH_4)_2RuCl_zBr_{6-z}$, where z is an integer from 1 to 5.

While neither desiring to be bound by any particular theory nor intending to limit in any measure the scope of the appended claims or their equivalents, it is presently believed that the yield of the hydrothermal reaction by which ruthenium refinery salt is converted to ruthenium intermediate increases with increasing concentration of the acid (e.g., hydrochloric acid). In addition, in view of the water solubility of the ruthenium intermediate, it is presently believed that the yield can be improved by washing the solid ruthenium intermediate product with an organic solvent instead of water. Representative organic solvents for use in accordance with the present teachings include but are not limited to aliphatic hydrocarbons (e.g., pentane, hexane, heptane, cyclohexane, etc.), esters (e.g., diethyl acetate, etc.), ketones (e.g., acetone, etc.), alcohols (e.g., methanol, ethanol, iso-propyl alcohol, etc.), aromatic hydrocarbons (e.g., benzene, toluene, xylenes, etc.), halogenated aromatic hydrocarbons (e.g., chlorobenzene, dichlorobenzene, etc.), halogenated alkanes (e.g., dichloromethane, chloroform, dichloroethane, etc.), ethers (e.g., dioxane, tetrahydrofuran, diethyl ether, tert-butyl methyl ether, dimethoxyethane, etc.), and the like, and combinations thereof. In some embodiments, the organic solvent used to wash the solid ruthenium intermediate product is cooled below room temperature prior to being used for the washing. In some embodiments, the organic solvent comprises acetone.

In some embodiments, the ruthenium refinery salt is one that is obtained from Refinery A, which was predetermined by XRD analysis to contain about 96.1 wt % $(NH_4)_4[Ru_2OCl_{10}]$ and about 3.9 wt % Ru metal impurity. In some embodiments, the Refinery A ruthenium refinery salt is converted to a ruthenium intermediate comprising $(NH_4)_2RuCl_6$—which, in some embodiments, appears as black crystals—via a hydrothermal treatment (150° C., 9 M HCl, 1.5 h) in yields of about 90 to about 95 percent (with about 4% of byproduct recovered by weight).

In some embodiments, the ruthenium refinery salt is one that is obtained from Refinery B, which was predetermined by XRD analysis to contain about 36.4 wt % $(NH_4)_4[Ru_2OCl_{10}]$, about 13.9 wt % $(NH_4)_2RuCl_5.H_2O$, and about 49.3 wt % $NH_4Cl$ impurity. In some embodiments, excess $NH_4Cl$ (about 40 wt %) is first removed from the Refinery B ruthenium refinery salt via sublimation. In some embodiments, the Refinery B ruthenium refinery salt remaining after sublimation is converted to a ruthenium intermediate comprising $(NH_4)_2RuCl_6$—which, in some embodiments, appears as black crystals—via a hydrothermal treatment (150° C., 9 M HCl, 2 h) in yields of about 82 to about 95 percent.

In some embodiments, the reacting of a ruthenium refinery salt with hydrogen halide to form a ruthenium intermediate comprises atmospheric conditions. In some embodiments, the reacting is performed in an open system. In some embodiments, the reacting is performed in an open system and the hydrogen halide is provided as an aqueous solution. In some embodiments, the hydrogen halide comprises hydrogen chloride, which in some embodiments is provided in aqueous solution as hydrochloric acid. In some embodiments, the hydrogen chloride is provided in aqueous solution as concentrated hydrochloric acid. In some embodiments, the hydrochloric acid has a concentration of at least about 6 M or higher. In some embodiments, the hydrochloric acid has a concentration of at least about 7 M or higher. In some embodiments, the hydrochloric acid has a concentration of at least about 8 M or higher. In some embodiments, the hydrochloric acid has a concentration of at least about 9 M or higher. In some embodiments, the reacting comprises refluxing the ruthenium refinery salt in concentrated hydrochloric acid. In some embodiments, the hydrogen halide comprises hydrogen bromide, which in some embodiments is provided in aqueous solution as hydrobromic acid. In some embodiments, the reacting comprises refluxing the ruthenium refinery salt in concentrated hydrobromic acid.

In some embodiments, the reacting under atmospheric conditions comprises refluxing the ruthenium refinery salt in an aqueous solution of a hydrogen halide. In some embodiments, the reacting under atmospheric conditions comprises refluxing the ruthenium refinery salt in hydrochloric acid (e.g., 7 M, 8 M, 9 M or concentrated) for at least 5 hours, in some embodiments for at least 6 hours, and in some embodiments for at least 7 or more hours. In some embodiments, the ruthenium intermediate obtained by the atmospheric synthesis is a black solid. However, the ruthenium intermediate product produced under atmospheric conditions does not always appear to be black. In some embodiments, the yields of ruthenium intermediate obtained by atmospheric synthesis are about 80 to about 90 percent.

Either atmospheric or hydrothermal conditions can be used for the conversion of a ruthenium refinery salt to a ruthenium intermediate in accordance with the present teachings. In some embodiments, hydrothermal conditions may be desirable (e.g., to increase reproducibility of the conversion). In some embodiments, atmospheric conditions may be desirable (e.g., in larger scale reactions for which an appropriately sized Parr-type reactor is not readily available).

In some embodiments, the ruthenium intermediate formed from the reaction of a ruthenium refinery salt with hydrogen halide comprises one or a plurality of ammonium cations and/or one or a plurality of halide ligands. In some embodiments, the hydrogen halide comprises hydrogen chloride, and the ruthenium intermediate formed from the reaction of a ruthenium refinery salt with hydrogen chloride comprises one or a plurality of ammonium cations and/or one or a plurality of chloride ligands. In some embodiments, the ruthenium intermediate further comprises one or a plurality of additional halide ligands other than chloride. In some embodiments, the ruthenium intermediate comprises a compound selected from the group consisting of $(NH_4)_2RuCl_6$, $(NH_4)_3RuCl_6$, $(NH_4)_2RuCl_5.H_2O$, $(NH_3)_6RuCl_3$, $(NH_4)_2RuBr_6$, $(NH_4)_2RuCl_zBr_{6-z}$, wherein z is an integer from 1 to 5, and combinations thereof.

In some embodiments, the ruthenium intermediate comprises a compound selected from the group consisting of $(NH_4)_2RuCl_6$, $(NH_4)_2RuBr_6$, $(NH_4)_2RuCl_zBr_{6-z}$, wherein z is an integer from 1 to 5, and combinations thereof. In some embodiments, the ruthenium intermediate comprises a compound having a structure $(NH_4)_2RuCl_6$. In some embodiments, at least a portion of the $(NH_4)_2RuCl_6$ is crystalline. In other embodiments, at least a portion of the $(NH_4)_2RuCl_6$ is a powder. In some embodiments, the $(NH_4)_2RuCl_6$ appears as black microcrystals. While neither desiring to be bound by any particular theory nor intending to limit in any measure the scope of the appended claims or their equivalents, it is presently believed that at least a portion of the $(NH_4)_2RuCl_6$ is crystalline when it has been prepared according to hydrothermal conditions, whereas at least a portion of the $(NH_4)_2RuCl_6$ is a powder when it has been prepared according to atmospheric conditions.

As further described in Example 12 below, samples of ruthenium intermediates obtained from the hydrothermal and atmospheric treatments of a ruthenium refinery salt with hydrochloric acid were examined by XRD analysis and were found to be comprised primarily of $(NH_4)_2RuCl_6$. Depending on the conditions under which the ruthenium intermediate was formed, the samples were found to contain varying amounts of impurities including $(NH_4)_4[Ru_2OCl_{10}]$ and Ru metal.

In some embodiments, the ruthenium intermediate obtained from the hydrothermal and/or atmospheric treatment of a ruthenium refinery salt in accordance with the present teachings is reacted with an olefin to form a ruthenium carbene complex precursor. In some embodiments, the olefin is cyclic. In some embodiments, the cyclic olefin is selected from the group consisting of cyclohexadiene, cycloheptadiene, cyclooctadiene, cyclononadiene, cyclodecadiene, cycloundecadiene, cyclododecadiene, cyclododecatriene, all stereoisomers thereof, and the like, and combinations thereof. In some embodiments, the cyclic olefin is selected from the group consisting of cyclooctadiene, cyclododecatriene, and combinations thereof.

In some embodiments, about two equivalents of a cyclic olefin are reacted with a ruthenium intermediate to form a ruthenium carbene complex precursor in accordance with the present teachings. In some embodiments, about two equivalents of cyclooctadiene are reacted with a ruthenium intermediate to form a ruthenium carbene complex precursor in accordance with the present teachings. In some embodiments, the olefin (e.g., cyclooctadiene) is reacted with the ruthenium intermediate in an alcoholic solvent which, in some embodiments, can further serve as a reducing agent. Representative alcoholic solvents include but are not limited to aliphatic alcohols (e.g., methanol, ethanol, 1-propanol, iso-propanol, 1-butanol, sec-butanol, and the like, and combinations thereof), aromatic alcohols, polyols, and the like, and combinations thereof. In some embodiments, the cyclooctadiene reacted with the ruthenium intermediate comprises cis, cis-1,5-cyclooctadiene. In some embodiments, the ruthenium intermediate comprises $(NH_4)_2RuCl_6$, the cyclooctadiene comprises cis, cis-1,5-cyclooctadiene, and the reacting comprises refluxing the $(NH_4)_2RuCl_6$ and cis, cis-1,5-cyclooctadiene in an aliphatic alcoholic solvent. In some embodiments, the reaction of the ruthenium intermediate with cis, cis-1,5-cyclooctadiene to form a ruthenium carbene complex precursor is conducted in ethanol. In some embodiments, the yield of the reaction is higher in ethanol than in butanol, methanol or iso-propanol.

In some embodiments, a ruthenium intermediate $(NH_4)_2RuCl_6$ prepared under hydrothermal conditions is reacted with cyclooctadiene to form a ruthenium carbene complex precursor. In other embodiments, a ruthenium intermediate $(NH_4)_2RuCl_6$ prepared under atmospheric conditions is reacted with cyclooctadiene to form a ruthenium carbene complex precursor. While neither desiring to be bound by any particular theory nor intending to limit in any measure the scope of the appended claims or their equivalents, it is presently observed that (a) the yield of ruthenium carbene complex precursor from the reaction of ruthenium intermediate with cyclooctadiene increases (e.g., from about 33% to about 62%) as reaction time increases (e.g., from about 7 hours to about 30 hours), (b) the yield of the ruthenium carbene complex precursor does not change significantly when the amount of cyclooctadiene is increased from 2 equivalents to 3 equivalents, (c) using a ruthenium intermediate $(NH_4)_2RuCl_6$ prepared under hydrothermal conditions yields the same ruthenium carbene complex precursor as does using a ruthenium intermediate $(NH_4)_2RuCl_6$ prepared under atmospheric conditions, and (d) the reaction between ruthenium intermediate and cyclooctadiene proceeds to the same yield regardless of whether it is conducted in air or in a nitrogen atmosphere.

Figure 3:
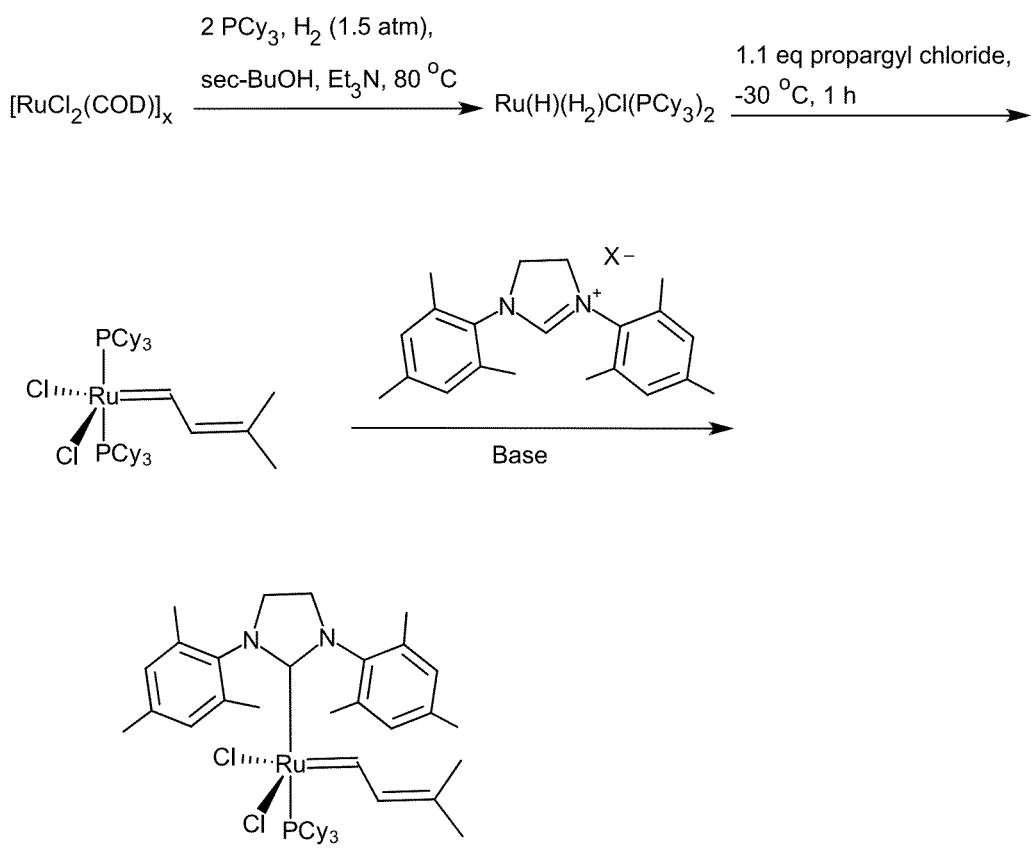
FIG. 3 shows a synthetic scheme for converting the ruthenium carbene complex precursor $[RuCl_2(COD)]_x$ to a Grubbs-type olefin metathesis catalyst.

In some embodiments, as shown in FIG. 3, the ruthenium carbene complex precursor comprises a material having a structure $[RuCl_2(COD)]_x$, wherein x is an integer value of 1 or more. In some embodiments, the $[RuCl_2(COD)]_x$ is polymeric. In some embodiments, the $[RuCl_2(COD)]_x$ appears as a yellowish-brownish solid.

In some embodiments, as shown in FIG. 3, a method for preparing a ruthenium vinylcarbene complex comprises converting a ruthenium carbene complex precursor prepared in accordance with the present teachings into a ruthenium hydrido halide complex, and reacting the ruthenium hydrido halide complex with a propargyl halide to form the ruthenium vinylcarbene complex. In some embodiments, the vinylcarbene complex constitutes a first-generation Grubbs-type olefin metathesis catalyst. In some embodiments, as shown in FIG. 3, the converting of the ruthenium carbene complex precursor into the ruthenium hydrido halide complex comprises reacting the ruthenium carbene complex precursor with a trialkyl phosphine, hydrogen, and a trialkyl amine as described, for example, in *Organometallics*, 1997, 16, No. 18, 3867-3869.

In some embodiments, the ruthenium hydrido halide complex comprises a compound having a structure $[Ru(H)(H_2)X(PR^1R^2R^3)_2]$, wherein X is a halide and wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. In some embodiments, covalent bonds may optionally exist between two or more of $R^1$, $R^2$, and $R^3$, such that when two or more of $R^1$, $R^2$, and $R^3$ are taken together, a bidentate ligand to phosphorous is formed. In some embodiments, the $C_1$-$C_{10}$ alkyl group is primary alkyl, secondary alkyl or cycloalkyl. In some embodiments, the cycloalkyl is cyclohexyl (Cy). In some embodiments, the ruthenium hydrido halide complex comprises a compound having a structure $[Ru(H)(H_2)Cl(PCy_3)_2]$. In some embodiments, the propargyl halide comprises 3-chloro-3-methyl-1-butyne. In some embodiments, as shown in FIG. 3, the ruthenium vinylcarbene complex prepared from the ruthenium carbene complex precursor comprises a compound having a structure $(PCy_3)_2Cl_2Ru=CH-CH=C(CH_3)_2$.

In some embodiments, the above-described method for preparing a ruthenium vinylcarbene complex further comprises replacing a phosphorous-containing ligand of the ruthenium vinylcarbene complex [Ru(H)(H$_2$)X(PR$^1$R$^2$R$^3$)$_2$] with an N-heterocyclic carbene ligand as described, for example, in U.S. Pat. No. 7,329,758 B1. In some embodiments, a phosphorous-containing ligand of the ruthenium vinylcarbene complex (e.g., a trialkyl phosphine ligand) is replaced with an imidazolidine ligand to form an imidazolidine-containing ruthenium vinylcarbene complex. In some embodiments, as shown in FIG. 3, the imidazolidine ligand comprises 1,3-dimesityl-4,5-dihydroimidazole. In some embodiments, the imidazolidine-containing ruthenium vinylcarbene complex constitutes a second-generation Grubbs-type olefin metathesis catalyst.

In some embodiments, the ruthenium intermediate obtained from the hydrothermal and/or atmospheric treatment of a ruthenium refinery salt in accordance with the present teachings is reacted with a phosphorous-containing material (e.g., a phosphine and/or phosphite) to form a ruthenium carbene complex precursor. In some embodiments, the phosphorous-containing material comprises a structure PR$^1$R$^2$R$^3$, wherein R$^1$, R$^2$, and R$^3$ are alike or different and are each independently selected from the group consisting of substituted or unsubstituted aryl, substituted or unsubstituted C$_1$-C$_{10}$ alkyl, substituted or unsubstituted aryloxy, substituted or unsubstituted C$_1$-C$_{10}$ alkoxy, and combinations thereof. In some embodiments, covalent bonds may optionally exist between two or more of R$^1$, R$^2$, and R$^3$, such that when two or more of R$^1$, R$^2$, and R$^3$ are taken together, a bidentate ligand to phosphorous is formed. In some embodiments, one or more of R$^1$, R$^2$, and R$^3$ comprises phenyl. In some embodiments, each of R$^1$, R$^2$, and R$^3$ comprises phenyl. In some embodiments, one or more of R$^1$, R$^2$, and R$^3$ comprises cycloalkyl (e.g., cyclohexyl). In some embodiments, each of R$^1$, R$^2$, and R$^3$ comprises cycloalkyl (e.g., cyclohexyl). In some embodiments, the ruthenium intermediate obtained from the hydrothermal and/or atmospheric treatment of a ruthenium refinery salt with hydrogen chloride in accordance with the present teachings is reacted with three equivalents of a phosphorous-containing material (e.g., a phosphine) to form a ruthenium carbene complex precursor comprising a structure RuCl$_2$(PR$^1$R$^2$R$^3$)$_3$, wherein R$^1$, R$^2$, and R$^3$ are alike or different and are each independently selected from the group consisting of substituted or unsubstituted aryl, substituted or unsubstituted C$_1$-C$_{10}$ alkyl, substituted or unsubstituted aryloxy, substituted or unsubstituted C$_1$-C$_{10}$ alkoxy, and combinations thereof. In some embodiments, covalent bonds may optionally exist between two or more of R$^1$, R$^2$, and R$^3$, such that when two or more of R$^1$, R$^2$, and R$^3$ are taken together, a bidentate ligand to phosphorous is formed.

Figure 5:
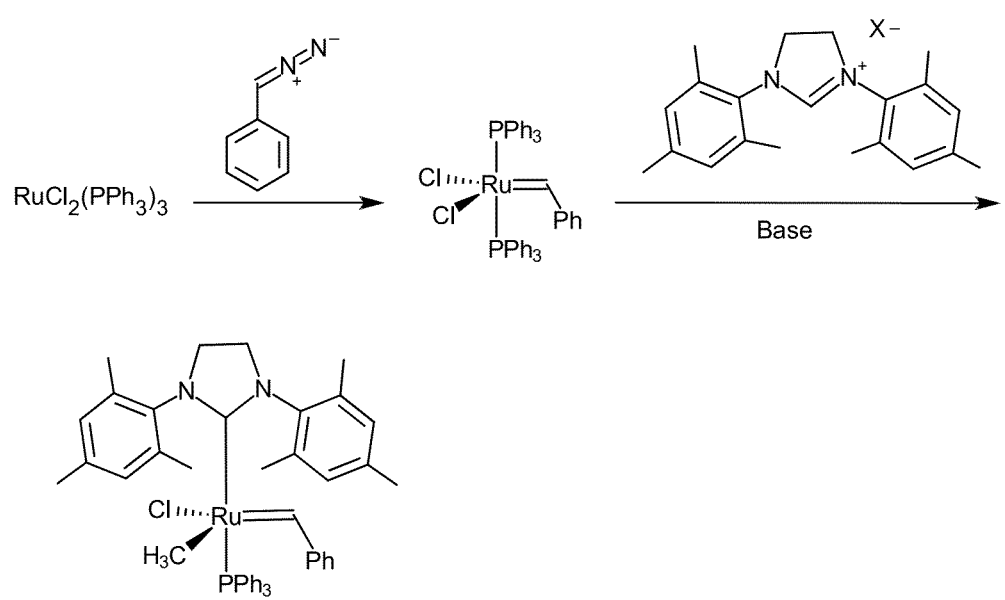
FIG. 5 shows a synthetic scheme for converting the ruthenium carbene complex precursor $RuCl_2(PPh_3)_3$ to a Grubbs-type olefin metathesis catalyst.

In some embodiments, as shown in FIG. 5, a method for preparing a ruthenium carbene complex comprises converting a ruthenium carbene complex precursor prepared in accordance with the present teachings into a ruthenium carbene complex having a structure (PR$^1$R$^2$R$^3$)$_2$Cl$_2$Ru=CH—R$^4$, wherein R$^1$, R$^2$, R$^3$, and R$^4$ are alike or different and are each independently selected from the group consisting of substituted or unsubstituted aryl, substituted or unsubstituted C$_1$-C$_{10}$ alkyl, substituted or unsubstituted aryloxy, substituted or unsubstituted C$_1$-C$_{10}$ alkoxy, and combinations thereof. In some embodiments, covalent bonds may optionally exist between two or more of R$^1$, R$^2$, and R$^3$, such that when two or more of R$^1$, R$^2$, and R$^3$ are taken together, a bidentate ligand to phosphorous is formed. In some embodiments, one or more of R$^1$, R$^2$, R$^3$, and R$^4$ comprises phenyl. In some embodiments, each of R$^1$, R$^2$, R$^3$, and R$^4$ comprises phenyl. In some embodiments, one or more of R$^1$, R$^2$, R$^3$, and R$^4$ comprises cycloalkyl (e.g., cyclohexyl). In some embodiments, each of R$^1$, R$^2$, R$^3$, and R$^4$ comprises cycloalkyl (e.g., cyclohexyl). In some embodiments, the carbene complex constitutes a first-generation Grubbs-type olefin metathesis catalyst. In some embodiments, as shown in FIG. 5, the converting of the ruthenium carbene complex precursor into a ruthenium carbene complex comprises reacting the ruthenium carbene complex precursor with phenyldiazomethane as described, for example, in J. Am. Chem. Soc., 1996, 118, 100.

In some embodiments, as shown in FIG. 5, the above-described method for preparing a ruthenium carbene complex further comprises replacing a phosphorous-containing ligand of the ruthenium carbene complex (e.g., a phosphine) with an N-heterocyclic carbene ligand to form an N-heterocyclic carbene-containing ruthenium carbene complex. In some embodiments, a phosphorous-containing ligand of the ruthenium carbene complex is replaced with an imidazolidine ligand to form an imidazolidine-containing ruthenium carbene complex. In some embodiments, as shown in FIG. 5, the imidazolidine ligand comprises 1,3-dimesityl-4,5-dihydroimidazole. In some embodiments, the imidazolidine-containing ruthenium carbene complex constitutes a second-generation Grubbs-type olefin metathesis catalyst.

By way of illustration, as shown in FIGS. 3 and 5, ruthenium carbene complex precursors such as [RuCl$_2$(COD)]$_x$ and RuCl$_2$(PPh$_3$)$_3$ prepared in accordance with the present teachings can be readily transformed into ruthenium carbene complexes for use as olefin metathesis catalysts (e.g., first- and/or second-generation Grubbs-type metathesis catalysts). Moreover, in contrast to conventional methodology, the present teachings circumvent costly conversions of ruthenium refinery salts to ruthenium metal and subsequent oxidation of ruthenium metal to RuCl$_3$. In addition, the present teachings are in no way limited to the ruthenium feedstock from a particular refinery, and salts from other refineries in addition to the A and B refineries referenced herein may be employed.

The following examples and representative procedures illustrate features in accordance with the present teachings, and are provided solely by way of illustration. They are not intended to limit the scope of the appended claims or their equivalents.

EXAMPLES

Materials

Unless otherwise indicated, all chemicals were used as received and without drying. Ruthenium refinery salt was purchased from Refineries A and B. Ethanol (200 proof, absolute), hydrochloric acid (37%), hydrobromic acid (48%), and cis,cis-1,5-cyclooctadiene (>98% pure) were purchased from Sigma Aldrich.

Example 1

XRD Analysis of Refinery A Ruthenium Refinery Salt

A sample of a Refinery A ruthenium refinery salt was examined by XRD analysis as received. The x-ray powder patterns were measured (Cu K$_\alpha$ radiation, 5-100° 2θ, 0.0202144° steps, 1 sec/step) on a Bruker D2 Phaser diffractometer equipped with a LynxEye position-sensitive detector. Quantitative analysis of the crystalline phases was carried out by the Rietveld method using GSAS.

The Refinery A ruthenium refinery salt was determined to contain (NH$_4$)$_4$[Ru$_2$OCl$_{10}$] and 3.9(1) wt % Ru metal impurity. The compound was identified by indexing the pattern on a high-quality body-centered tetragonal unit cell, and using lattice matching techniques to find the K analog (*Acta Cryst. B*, 1979, 35, 558-561). The structure was refined, as shown in Table 1, and hydrogens placed in approximate positions. An acceptable Rietvald refinement was obtained.

TABLE 1

Refined Atom Coordinates of $(NH_4)_4[Cl_5RuORuCl_5]$
Space Group = I 4/m m m
Lattice constants are a = 7.30369(11); b = A; c = 17.0938(4);
Alpha = 90; Beta = 90; Gamma = 90; Cell volume = 911.850(28)

| Name | X | Y | Z | Ui/Ue*100 | Site sym | Mult | Type | Seq | Fractn |
|---|---|---|---|---|---|---|---|---|---|
| Ru1 | 0.000000 | 0.000000 | 0.10779(18) | 2.14 | 4MM(001) | 4 | RU | 1 | 1.0000 |
| Cl2 | 0.22958(28) | 0.22958(28) | 0.11396(26) | 2.12 | M(+−0) | 16 | CL | 2 | 1.0000 |
| Cl3 | 0.000000 | 0.000000 | 0.24535(44) | 2.12 | 4MM(001) | 4 | CL | 3 | 1.0000 |
| O4 | 0.000000 | 0.000000 | 0.000000 | 3.00 | 4/MMM001 | 2 | O | 4 | 1.0000 |
| N5 | 0.000000 | 0.500000 | 0.250000 | 3.00 | −4M2 001 | 4 | N | 5 | 1.0000 |
| N6 | 0.000000 | 0.500000 | 0.000000 | 3.00 | MMM | 4 | N | 6 | 1.0000 |
| H7 | 0.056070 | 0.433980 | 0.216790 | 5.00 | 1 | 32 | H | 7 | 0.5000 |
| H8 | 0.060210 | 0.557780 | 0.029880 | 5.00 | 1 | 32 | H | 8 | 0.5000 |

Example 2

XRD Analysis of Refinery B Ruthenium Refinery Salt

A sample of Refinery B ruthenium refinery salt was first ground with a mortar and pestle prior to analysis but an acceptable powder pattern was not obtained from the damp solid. A portion was ground as an acetone slurry with a mortar and pestle, which resulted in a better powder pattern. The x-ray powder patterns were measured (Cu $K_\alpha$ radiation, 5-100° 2θ, 0.0202144° steps, 1 sec/step) on a Bruker D2 Phaser diffractometer equipped with a LynxEye position-sensitive detector. Quantitative analysis of the crystalline phases was carried out by the Rietveld method using GSAS.

The Refinery B ruthenium refinery salt was determined to contain a mixture of 36.4(2) wt % $(NH_4)_4[Ru_2OCl_{10}]$, 49.6(2) wt % $NH_4Cl$, and 13.9(2) wt % $(NH_4)_2RuCl_5.H_2O$. The $(NH_4)_4[Ru_2OCl_{10}]$ exhibits significant preferred orientation (texture index=2.02, reflecting difficulty in grinding the large grains to obtain a random powder. The $(NH_4)_2RuCl_5.H_2O$ was identified by analogy to several $(NH_4)_2RuCl_5X$ compounds. At present, the powder pattern is not yet in the Powder Diffraction File but the crystal structure has been reported (*Zh. Strukt. Khim.*, 2008, 49, 585-588; ICSD collection code 411727). The $(NH_4)_4[Ru_2OCl_{10}]$ in the Refinery B sample exhibits a larger degree of strain broadening than the Refinery A sample.

The phase composition for the Refinery B salt corresponds to a bulk analysis of $C_{0.0}H_{32.51}N_{8.00}O_{0.63}Ru_{1.0}Cl_{11.00}$ compared to the measured $C_{0.09}H_{19.68}N_{5.20}O_{1.30}Ru_{1.0}Cl_{8.43}$. While neither desiring to be bound by any particular theory nor intending to limit in any measure the scope of the appended claims or their equivalents, it is presently believed that the preferred orientation/granularity may have distorted the quantitative analysis and/or that the sample contains some amorphous material.

Example 3

Removal of $NH_4Cl$ from Refiner B Ruthenium Refine Salt by Sublimation

In a sublimator, 7.5 g of Refinery B ruthenium salt was sublimed in vacuo (0.05 Torr), at 150-200° C. for 6 hours. $NH_4Cl$ sublimes onto the cold finger (−5° C.) (2.2 g) while the Ru salts remain below (4.3 g). Ruthenium salt remaining after sublimation is determined to be $(NH_4)_4[Ru_2OCl_{10}]$ and $(NH_4)_2RuCl_5.H_2O$ by elemental analysis and IR spectroscopy. Ru wt %=32.9% up from 18.8% in raw salt.

Example 4

Hydrothermal Treatment of Sublimed Refinery B Ruthenium Refinery Salt

In a 23-mL Parr reactor, sublimed Refinery B ruthenium refinery salt (1.0660 g) and 6 M HCl (10 mL) were heated to 150° C. for 6 hours. The resulting solution was filtered at room temperature and black microcrystals remained on the filter paper. The microcrystals were washed with water. Elemental analysis confirmed that the black microcrystalline product was $(NH_4)_2RuCl_6$ (0.63 g).

Example 5

Preparation of Ruthenium Carbene Complex Precursor $[RuCl_2(COD)]_x$ from Refinery B-Derived Ruthenium Intermediate In a 200-mL 3-necked flask fitted with an inlet, a condenser, a bubbler, and a stopper, $(NH_4)_2RuCl_6$ (1.57 g, product from hydrothermal treatment of a Refinery B salt), cis,cis-1,5-cyclooctadiene (1.48 g, 3 eq.), and ethanol (45 mL) were refluxed for 6 hours under $N_2$. The solid was insoluble in ethanol; however, there was a color change from black to rusty brown. The solid was filtered at ambient temperature through a Buchner funnel and washed with ethanol. The isolated rusty brown solid was then washed with $H_2O$ (100 mL) yielding a yellowish brown solid, $[RuCl_2(COD)]_x$ (0.2126 g).

Example 6

Hydrothermal Treatment of Refinery A Ruthenium Refinery Salt

In a 23-mL Parr reactor, Refinery A ruthenium refinery salt (1 g) and 6 M HCl (10 mL) were heated to 150° C. for 6 hours. The resulting solution was filtered at room temperature and black microcrystals remained on the filter paper. The microcrystals were washed with water. Elemental analysis confirmed that the black microcrystalline product was $(NH_4)_2RuCl_6$ (0.6 g).

Example 7

Hydrothermal Treatment of Refinery A Ruthenium Refinery Salt

In a 23-mL Parr reactor, Refinery A ruthenium refinery salt (1 g) and 9 M HCl (5 mL) were heated to 150° C. for 2 hours. The resulting solution was filtered at room temperature and black microcrystals remained on the filter paper. The microcrystals were washed with acetone. Elemental analysis confirmed that the black microcrystalline product was $(NH_4)_2RuCl_6$ (1.1 g).

Example 8

Atmospheric Treatment of Refinery A Ruthenium Refinery Salt

In a 100-mL round-bottomed flask fitted with a condenser, Refinery A ruthenium refinery salt (3.0302 g) and concentrated HCl (37%, 30 mL) were refluxed at 100° C. for 6 hours. The resulting solution was filtered at room temperature in a Buchner funnel, and a fine black solid, $(NH_4)_2RuCl_6$ (2.5118 g) was washed with water and recovered from the filter paper.

Example 9

Atmospheric Treatment of Refinery A Ruthenium Refinery Salt

In a 200-mL 3-necked flask fitted with $N_2$ purge and a condenser, Refinery A ruthenium refinery salt (5 g) and concentrated HBr (50 mL) were refluxed for 6 h. A bluish-black solid (7.6 g) was filtered out of the solution at room temperature using a Buchner funnel and washed with acetone. Elemental analysis confirmed that a majority of the solid product is $(NH_4)_2RuBr_6$ (yield about 80%) with about 1.2 wt % chlorine present. The chlorine may stem from $(NH_4)_2RuCl_zBr_{6-z}$, where z is an integer from 1 to 5, and/or from unreacted $(NH_4)_4[Ru_2OCl_{10}]$ starting material present in the sample.

Example 10

Preparation of Ruthenium Carbene Complex Precursor $[RuCl_2(COD)]_x$ from Refinery A-Derived Ruthenium Intermediate In a 200-mL 3-necked flask fitted with an inlet, a condenser, a bubbler, and a stopper, $(NH_4)_2RuCl_6$ (1.13 g, product from hydrothermal treatment of a Refinery A salt), cis, cis-1,5-cyclooctadiene (1.05 g, 3 eq.), and ethanol (30 mL) were refluxed for 6 hours under $N_2$. The solid was insoluble in ethanol; however, there was a color change from black to rusty brown. The solid was filtered at ambient temperature through a Buchner funnel and washed with ethanol. The isolated rusty brown solid was then washed with $H_2O$ (100 mL) yielding a yellowish brown solid, $[RuCl_2(COD)]_x$ (0.2977 g).

Figure 6:
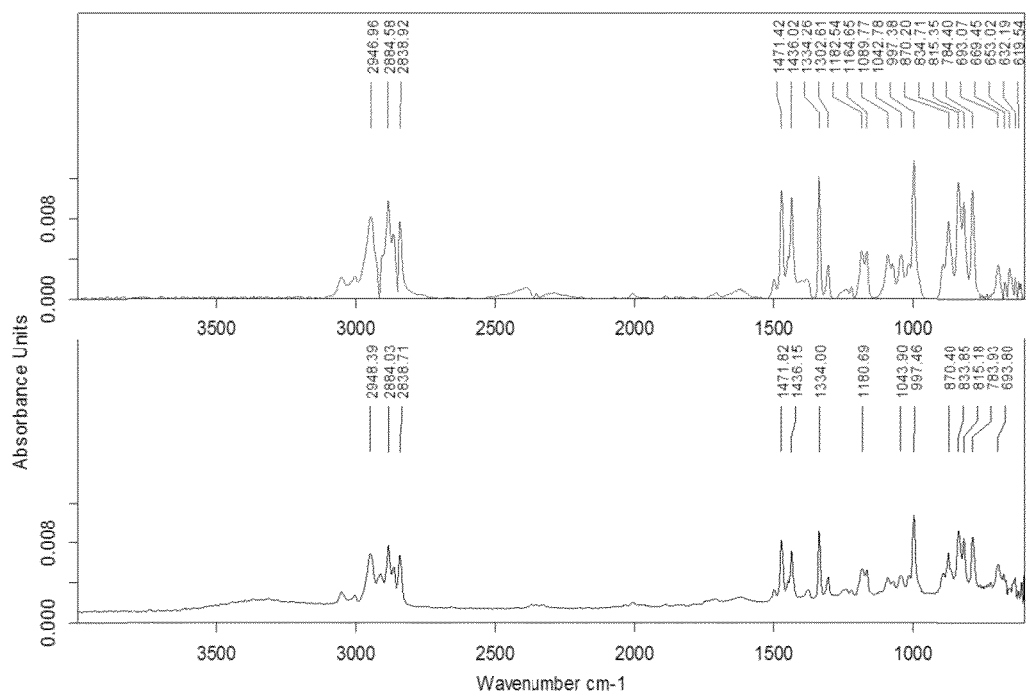
FIG. 6 shows the infrared spectra of $[RuCl_2(COD)]_x$ prepared in accordance with the present teachings (top spectrum) and commercially available $[RuCl_2(COD)]_x$ purchased from Strem Chemicals, Inc. (bottom spectrum).

As shown in FIG. 6, the IR spectrum of synthesized $[RuCl_2(COD)]_x$ (top spectrum) prepared from a Refinery A salt as described above matches that of commercially available $[RuCl_2(COD)]_x$ from Strem Chemicals, Inc. (Newburyport, Mass.) (bottom spectrum). Moreover, an equivalent product is obtained when the $[RuCl_2(COD)]_x$ is prepared from Refinery B salt (after its purification via sublimation). Thus, a viable synthesis of $[RuCl_2(COD)]_x$—a precursor to ruthenium carbene complexes, such as those used as catalysts in olefin metathesis—from low-cost ruthenium refinery salts via the intermediacy of $(NH_4)_2RuCl_6$ has been demonstrated.

Example 11

Preparation of Ruthenium Carbene Complex Precursor $[RuCl_2(COD)]_x$ from Refinery A-Derived Ruthenium Intermediate In a 200-mL 3-necked flask fitted with an inlet, a condenser, a bubbler, and a stopper, $(NH_4)_2RuCl_6$ (3.03 g, product from hydrothermal treatment of a Refinery A salt), cis, cis-1,5-cyclooctadiene (1.96 g, 2 eq.), and ethanol (45 mL) were refluxed for 30 hours under $N_2$. The solid was insoluble in ethanol; however, there was a color change from black to rusty brown. The solid was filtered at ambient temperature through a Buchner funnel and washed with ethanol. The isolated rusty brown solid was then washed with $H_2O$ (250 mL) yielding a yellowish brown solid, $[RuCl_2(COD)]_x$ (1.56 g).

Example 12

XRD Analysis of Ruthenium Intermediates Obtained from Hydrothermal and Atmospheric Treatments of Refinery A Ruthenium Refinery Salt A sample of a ruthenium intermediate obtained from the atmospheric treatment of a Refinery A refinery salt was examined by XRD analysis as received. A sample of a ruthenium intermediate obtained from the hydrothermal treatment of a Refinery A ruthenium refinery salt was ground with a mortar and pestle prior to analysis.

The x-ray powder patterns were measured (Cu $K_\alpha$ radiation, 5-100° 2θ, 0.0202144° steps, 0.5 sec/step) on a Bruker D2 Phaser diffractometer equipped with a LynxEye position-sensitive detector. Quantitative analysis of the crystalline phases was carried out by the Rietveld method using GSAS.

The x-ray powder pattern of the major phase in both samples matches that of several face-centered cubic $(NH_4)_2MCl_6$ compounds. Accordingly, this phase was identified as $(NH_4)_2RuCl_6$. Since the crystal structure of $(NH_4)_2RuCl_6$ was not previously refined, although some of its thermodynamic properties have been reported in the literature (*J. Chem Thermodynamics*, 2002, 34, 133-153), the structure of $(NH_4)_2ReCl_6$ was used as the initial model for the refinement, as shown in Table 3.

TABLE 3

| Refined Crystal Structure of $(NH_4)_2RuCl_6$ Space Group = Fm3m, a = 9.86201 (13) Å | | | | |
|---|---|---|---|---|
| ATOM | x | y | z | $U_{iso}$, Å$^2$ |
| Ru1 | 0 | 0 | 0 | 0.0241(7) |
| Cl2 | 0.2361(2) | 0 | 0 | 0.0255(8) |
| N3 | ¼ | ¼ | ¼ | 0.03 |
| H4 | 0.3072 | 0.3072 | 0.3072 | 0.039 |

The displacement coefficient of the Cl is reasonable for a fully-occupied chlorine atom. Therefore, the compound is identified as $(NH_4)_2RuCl_6$ rather than $(NH_4)_2RuCl_5.H_2O$, which would yield a larger $U_{iso}$ for the Cl.

The phase composition data for the two samples are shown in Table 4. Both samples are comprised primarily of $(NH_4)_2RuCl_6$ but contain varying amounts of impurities including $(NH_4)_4[Ru_2OCl_{10}]$ and Ru metal. The hydrothermally-derived ruthenium intermediate has a lower concentration of impurities and was contains 94.3 wt % $(NH_4)_2RuCl_6$, 0.9 wt % $(NH_4)_4[Ru_2OCl_{10}]$, and 4.9 wt % Ru metal. The atmospherically-derived ruthenium intermediate appears to have some amorphous material (from a broad feature in the background at approximately 16° 2θ), and contains 83.5 wt % $(NH_4)_2RuCl_6$, 10 wt % $(NH_4)_4[Ru_2OCl_{10}]$, and 6.4 wt % Ru metal.

TABLE 4

Phase Compositions of Ruthenium Intermediate Samples

| | Hydrothermally-Derived Ruthenium Intermediate | Atmospherically-Derived Ruthenium Intermediate |
|---|---|---|
| $(NH_4)_2RuCl_6$, wt % | 94.3 (1) | 83.5 (1) |
| a, Å | 9.8637 (2) | 9.8620 (1) |
| Profile U | 17.2 (49) | 51 (3) |
| Profile Y | 16.4 (4) | 4.8 (4) |
| strain, % | 0.25 (1) | 0.05 (1) |
| $(NH_4)_4[Ru_2OCl_{10}]$, wt % | 0.9 (1) | 10.0 (1) |
| Ru, wt % | 4.9 (1) | 6.4 (1) |
| Profile X | 5.8 (3) | 6.3 (2) |
| size, Å | 2500 (200) | 2200 (100) |
| other | | amorphous |

The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A method for preparing a ruthenium carbene complex precursor comprising:
    (a) reacting a ruthenium refinery salt with a hydrogen halide to form a ruthenium intermediate, the ruthenium refinery salt being a salt of a halogen-containing ruthenium complex; wherein the hydrogen halide comprises hydrogen chloride, hydrogen bromide, or combinations thereof; and wherein the halogen-containing ruthenium complex comprises halogen atoms selected from the group consisting of chlorine and bromine; and
    (b) reacting the ruthenium intermediate with an L-type ligand to form the ruthenium carbene complex precursor.

2. The invention of claim 1 wherein the L-type ligand is selected from the group consisting of olefins, phosphines, phosphites, amines, CO, $N_2$, and combinations thereof.

3. The invention of claim 1 wherein the L-type ligand is selected from the group consisting of olefins, phosphines, and a combination thereof.

4. The invention of claim 1 wherein the L-type ligand comprises a cyclic olefin.

5. The invention of claim 4 wherein the cyclic olefin is selected from the group consisting of a diene, a triene, and a combination thereof.

6. The invention of claim 4 wherein the cyclic olefin is selected from the group consisting of cyclohexadiene, cycloheptadiene, cyclooctadiene, cyclononadiene, cyclodecadiene, cycloundecadiene, cyclododecadiene, cyclododecatriene, paramenthadiene, phellandrene, norbornadiene, terpinene, limonene, and combinations thereof.

7. The invention of claim 4 wherein the cyclic olefin is selected from the group consisting of cyclooctadiene, cyclododecatriene, and combinations thereof.

8. The invention of claim 4 wherein the cyclic olefin comprises cyclooctadiene.

9. The invention of claim 1 wherein the L-type ligand comprises a phosphorous-containing ligand having a structure $PR^1R^2R^3$;
    wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof; and
    wherein covalent bonds may optionally exist between two or more of $R^1$, $R^2$, and $R^3$, such that when two or more of $R^1$, $R^2$, and $R^3$ are taken together, a bidentate ligand to phosphorous is formed.

10. The invention of claim 9 wherein the phosphorous-containing ligand comprises triphenyl phosphine.

11. The invention of claim 1 wherein the hydrogen halide comprises hydrogen chloride.

12. The invention of claim 1 wherein the hydrogen halide comprises hydrogen bromide.

13. The invention of claim 1 wherein the hydrogen halide comprises hydrogen chloride and wherein the L-type ligand comprises a cyclic olefin.

14. The invention of claim 13 wherein the cyclic olefin comprises cyclooctadiene.

15. The invention of claim 1 wherein the ruthenium refinery salt comprises a material selected from the group consisting of $(NH_4)_2RuCl_5$, $(NH_4)_2RuCl_5.H_2O$, polyhydrated $(NH_4)_2RuCl_5$, $(NH_4)_4[Ru_2OCl_{10}]$, and combinations thereof.

16. The invention of claim 15 wherein the ruthenium refinery salt further comprises $NH_4Cl$.

17. The invention of claim 16 wherein the method further comprises removing at least a portion of the $NH_4Cl$ from the ruthenium refinery salt prior to reacting the ruthenium refinery salt with the hydrogen halide.

18. The invention of claim 17 wherein at least a portion of the $NH_4Cl$ is removed via sublimation.

19. The invention of claim 18 wherein at least a portion of sublimed $NH_4Cl$ is removed from the ruthenium refinery salt prior to reacting the ruthenium refinery salt with the hydrogen halide.

20. The invention of claim 1 wherein the ruthenium intermediate comprises one or a plurality of ammonium cations and one or a plurality of halide ligands, the halide ligands being selected from the group consisting of chloride and bromide.

21. The invention of claim 1 wherein the ruthenium intermediate comprises one or a plurality of ammonium cations and one or a plurality of chloride ligands.

22. The invention of claim 21 wherein the ruthenium intermediate further comprises one or a plurality of bromide ligands.

23. The invention of claim 1 wherein the ruthenium intermediate comprises a compound having a structure $(NH_4)_2RuCl_6$.

24. The invention of claim 23 wherein at least a portion of the $(NH_4)_2RuCl_6$ is crystalline.

25. The invention of claim 23 wherein at least a portion of the $(NH_4)_2RuCl_6$ is a powder.

26. The invention of claim 11 wherein the hydrogen chloride is provided in aqueous solution as hydrochloric acid.

27. The invention of claim 26 wherein concentration of the hydrochloric acid is at least about 5 M or higher.

28. The invention of claim 26 wherein concentration of the hydrochloric acid is at least about 6 M or higher.

29. The invention of claim 6 wherein the reacting with the hydrogen halide comprises a hydrothermal treatment.

30. The invention of claim 23 wherein the hydrogen halide comprise hydrogen chloride, which is provided in aqueous solution as hydrochloric acid having a concentration of at least about 6 M, and wherein the reacting is performed in a closed system.

31. The invention of claim 30 wherein a reaction temperature in the closed system is at least about 100° C.

32. The invention of claim 31 wherein at least a portion of the $(NH_4)_2RuCl_6$ is crystalline.

33. The invention of claim 6 wherein the reacting with the hydrogen halide comprises atmospheric conditions.

34. The invention of claim 33 wherein the hydrogen halide comprises hydrogen chloride, which is provided in aqueous solution as concentrated hydrochloric acid, and wherein the reacting is performed in an open system.

35. The invention of claim 34 wherein the ruthenium refinery salt is refluxed in the concentrated hydrochloric acid.

36. The invention of claim 35 wherein the ruthenium intermediate comprises a compound having a structure $(NH_4)_2RuCl_6$, and wherein at least a portion of the $(NH_4)_2RuCl_6$ is a powder.

37. The invention of claim 14 wherein the ruthenium intermediate comprises a compound having a structure $(NH_4)_2RuCl_6$, and wherein the cyclooctadiene comprises cis, cis-1,5-cyclooctadiene.

38. The invention of claim 14 wherein the ruthenium intermediate comprises a compound having a structure $(NH_4)_2RuCl_6$, and wherein the reacting of the ruthenium intermediate with cyclooctadiene comprises refluxing the ruthenium intermediate and cis, cis-1,5-cyclooctadiene in ethanol.

39. The invention of claim 1 wherein the ruthenium carbene complex precursor comprises a material having a structure $[RuCl_2(COD)]_x$, wherein x is an integer value of 1 or more.

40. The invention of claim 1 wherein the ruthenium carbene complex precursor comprises a material having a structure $RuCl_2(PR^1R^2R^3)_3$;
wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof; and
wherein covalent bonds may optionally exist between two or more of $R^1$, $R^2$, and $R^3$, such that when two or more of $R^1$, $R^2$, and $R^3$ are taken together, a bidentate ligand to phosphorous is formed.

41. A method for preparing a ruthenium carbene complex precursor comprising:
reacting a ruthenium refinery salt with a hydrogen halide to form a ruthenium intermediate; and
reacting the ruthenium intermediate with cyclooctadiene and/or a phosphorous-containing material having a structure $PR^1R^2R^3$ to form the ruthenium carbene complex precursor;
wherein the ruthenium refinery salt comprises a material selected from the group consisting of $(NH_4)_2RuCl_5$, $(NH_4)_2RuCl_5 \cdot H_2O$, polyhydrated $(NH_4)_2RuCl_5$, $(NH_4)_4[Ru_2OCl_{10}]$, and combinations thereof;
wherein the ruthenium intermediate comprises a compound selected from the group consisting of $(NH_4)_2RuX^1_6$, $(NH_4)_2RuX^1_yX^2_{6-y}$, and a combination thereof;
wherein the ruthenium carbene complex precursor comprises a compound having a structure $[RuX^3X^4(COD)]_x$ and/or a compound having a structure $RuX^5X^6(PR^1R^2R^3)_3$;
wherein x is an integer value of 1 or more;
wherein $X^1$, $X^2$, $X^3$, $X^4$, $X^5$, and $X^6$ are halogen atoms that are each independently selected from the group consisting of F, Cl, Br, and I with a caveat that $X^1$ and $X^2$ are different;
wherein y is an integer value from 1 to 5;
wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof; and
wherein covalent bonds may optionally exist between two or more of $R^1$, $R^2$, and $R^3$, such that when two or more of $R^1$, $R^2$, and $R^3$ are taken together, a bidentate ligand to phosphorous is formed.

42. A method for preparing a ruthenium vinylcarbene complex comprising:
converting a ruthenium carbene complex precursor prepared according to the method of claim 4 into a ruthenium hydrido halide complex; and
reacting the ruthenium hydrido halide complex with a propargyl halide to form the ruthenium vinylcarbene complex.

43. The invention of claim 42 wherein the converting comprises reacting the ruthenium carbene complex precursor with a trialkyl phosphine, hydrogen, and a trialkyl amine.

44. The invention of claim 42 wherein the ruthenium hydrido halide complex comprises a compound having a structure $[Ru(H)(H_2)X(PR^1R^2R^3)_2]$;
wherein X is a halide;
wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof; and
wherein covalent bonds may optionally exist between two or more of $R^1$, $R^2$, and $R^3$, such that when two or more of $R^1$, $R^2$, and $R^3$ are taken together, a bidentate ligand to phosphorous is formed.

45. The invention of claim 42 wherein the ruthenium hydrido halide complex comprises a compound having a structure $[Ru(H)(H_2)Cl(PCy_3)_2]$,
and wherein the propargyl halide comprises 3-chloro-3-methyl-1-butyne.

46. The invention of claim 45 wherein the ruthenium vinylcarbene complex comprises a compound having a structure $(PCy_3)_2Cl_2Ru=CH-CH=C(CH_3)_2$.

47. The invention of claim 43 further comprising replacing a phosphine ligand of the ruthenium vinylcarbene complex with an N-heterocyclic carbene ligand.

48. The invention of claim 43 further comprising replacing a phosphine ligand of the ruthenium vinylcarbene complex with an imidazolidine ligand to form an imidazolidine-containing ruthenium vinylcarbene complex.

49. The invention of claim 48 wherein the imidazolidine-containing ruthenium vinylcarbene complex constitutes a second-generation Grubbs-type olefin metathesis catalyst.

50. The invention of claim 48 wherein the imidazolidine ligand comprises 1,3-dimesityl-4,5-dihydroimidazole.

51. A method for preparing a ruthenium carbene complex comprising:
  converting a ruthenium carbene complex precursor prepared according to the method of claim 9 into a ruthenium carbene complex having a structure $(PR^1R^2R^3)_2X^1X^2Ru=CH-R^4$;
  wherein $X^1$ and $X^2$ are halogen atoms that are each independently selected from the group consisting of Cl and Br;
  wherein $R^1$, $R^2$, $R^3$, and $R^4$ are alike or different, and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof; and
  wherein covalent bonds may optionally exist between two or more of $R^1$, $R^2$, and $R^3$, such that when two or more of $R^1$, $R^2$, and $R^3$ are taken together, a bidentate ligand to phosphorous is formed.

52. The invention of claim 51 wherein the ruthenium carbene complex precursor comprises a structure $RuCl_2(PR^1R^2R^3)_3$.

53. The invention of claim 51 wherein each of $R^1$, $R^2$, $R^3$, and $R^4$ comprises phenyl.

54. The invention of claim 51 wherein the converting comprises reacting the ruthenium carbene complex precursor with phenyldiazomethane.

55. The invention of claim 51 further comprising replacing a phosphorous-containing ligand of the ruthenium carbene complex with an N-heterocyclic carbene ligand to form an N-heterocyclic carbene-containing ruthenium carbene complex.

56. The invention of claim 51 further comprising replacing a phosphorous-containing ligand of the ruthenium carbene complex with an imidazolidine ligand to form an imidazolidine-containing ruthenium carbene complex.

57. A method for preparing a ruthenium complex comprising reacting a ruthenium refinery salt with a hydrogen halide to form the ruthenium complex, the ruthenium refinery salt being a salt of a halogen-containing ruthenium complex;
  wherein the hydrogen halide comprises hydrogen chloride, hydrogen bromide, or combinations thereof; and
  wherein the halogen-containing ruthenium complex comprises halogen atoms selected from the group consisting of chlorine and bromine.

58. The invention of claim 57 wherein the ruthenium complex comprises an $[RuX^1_yX^2_{6-y}]^{2-}$ anion, wherein $X^1$ and $X^2$ are halogen atoms that are each independently selected from the group consisting of Cl and Br, and wherein y is an integer value from 1 to 6.

59. The invention of claim 57 wherein the ruthenium complex comprises one or a plurality of ammonium cations and one or a plurality of halide ligands, the halide ligands being selected from the group consisting of chloride and bromide.

60. The invention of claim 57 wherein the ruthenium complex comprises one or a plurality of ammonium cations and one or a plurality of chloride ligands.

61. The invention of claim 57 wherein the ruthenium complex comprises a compound selected from the group consisting of $(NH_4)_2RuX^1_6$, $(NH_4)_2RuX^1_yX^2_{6-y}$, and a combination thereof; wherein $X^1$ and $X^2$ are halogen atoms that are each independently selected from the group consisting of Cl and Br; and wherein y is an integer value from 1 to 5.

62. The invention of claim 57 wherein the ruthenium complex comprises a compound selected from the group consisting of $(NH_4)_2RuCl_6$, $(NH_4)_2RuBr_6$, $(NH_4)_2RuCl_zBr_{6-z}$ wherein z is an integer from 1 to 5, and combinations thereof.

63. The invention of claim 57 wherein the hydrogen halide comprises hydrogen chloride.

64. The invention of claim 57 wherein the hydrogen halide comprises hydrogen bromide.

65. The invention of claim 57 wherein the ruthenium refinery salt comprises a material selected from the group consisting of $(NH_4)_2RuCl_5$, $(NH_4)_2RuCl_5 \cdot H_2O$, polyhydrated $(NH_4)_2RuCl_5$, $(NH_4)_4[Ru_2OCl_{10}]$, and combinations thereof.

66. The invention of claim 65 wherein the hydrogen chloride is provided in aqueous solution as hydrochloric acid.

67. The invention of claim 57 wherein the reacting with the hydrogen halide comprises a hydrothermal treatment.

68. The invention of claim 57 wherein the reacting with the hydrogen halide comprises atmospheric conditions.

69. The invention of claim 1 wherein the L-type ligand is selected from the group consisting of olefins, phosphines, and a combination thereof.

70. The invention of claim 1 wherein the L-type ligand comprises a cyclic olefin.

71. The invention of claim 70 wherein the cyclic olefin is selected from the group consisting of a diene, a triene, and a combination thereof.

72. The invention of claim 70 wherein the cyclic olefin is selected from the group consisting of cyclohexadiene, cycloheptadiene, cyclooctadiene, cyclononadiene, cyclodecadiene, cycloundecadiene, cyclododecadiene, cyclododecatriene, paramenthadiene, phellandrene, norbornadiene, terpinene, limonene, and combinations thereof.

73. The invention of claim 70 wherein the cyclic olefin is selected from the group consisting of cyclooctadiene, cyclododecatriene, and combinations thereof.

74. The invention of claim 70 wherein the cyclic olefin comprises 1,5-cyclooctadiene.

75. The invention of claim 1 wherein the ruthenium intermediate is a ruthenium (IV) hexahalo complex that comprises a $[RuX^1_yX^2_{6-y}]^{2-}$ anion, wherein $X^1$ and $X^2$ are halogen atoms that are independently selected from the group consisting of Cl and Br; and wherein y is an integer value from 1 to 6.

76. The invention of claim 75 wherein the L-type ligand is selected from the group consisting of olefins, phosphines, phosphites, amines, CO, $N_2$, and combinations thereof.

77. The invention of claim 1, wherein the ruthenium intermediate is a salt of a ruthenium (IV) hexahalo complex, wherein the halide ligands of the ruthenium (IV) hexahalo complex are selected from the group consisting of chloride and bromide.

78. The invention of claim 77, wherein the L-type ligand is selected from the group consisting of olefins, phosphines, phosphites, amines, CO, $N_2$, and combinations thereof.

* * * * *